United States Patent
Watanabe et al.

(10) Patent No.: US 11,667,945 B2
(45) Date of Patent: Jun. 6, 2023

(54) DETECTION METHOD AND DETECTION PROBE FOR COLIBACTIN AND COLIBACTIN-PRODUCING BACTERIA

(71) Applicant: SHIZUOKA PREFECTURE PUBLIC UNIVERSITY CORPORATION, Shizuoka (JP)

(72) Inventors: Kenji Watanabe, Shizuoka (JP); Yuta Tsunematsu, Shizuoka (JP); Michio Sato, Shizuoka (JP)

(73) Assignee: Shizuoka Prefecture Public University Corporation, Shizuoka (JP)

( * ) Notice: Subject to any disclaimer, the term of this patent is extended or adjusted under 35 U.S.C. 154(b) by 369 days.

(21) Appl. No.: 16/642,696

(22) PCT Filed: Aug. 27, 2018

(86) PCT No.: PCT/JP2018/031489
§ 371 (c)(1),
(2) Date: Jun. 1, 2020

(87) PCT Pub. No.: WO2019/044736
PCT Pub. Date: Mar. 7, 2019

(65) Prior Publication Data
US 2021/0010051 A1    Jan. 14, 2021

(30) Foreign Application Priority Data
Aug. 28, 2017 (JP) .............................. JP2017-163079

(51) Int. Cl.
| | | |
|---|---|---|
| G01N 33/53 | (2006.01) | |
| C12Q 1/04 | (2006.01) | |
| C07D 311/18 | (2006.01) | |
| C09K 11/07 | (2006.01) | |
| G01N 33/569 | (2006.01) | |

(52) U.S. Cl.
CPC .............. C12Q 1/04 (2013.01); C07D 311/18 (2013.01); C09K 11/07 (2013.01); G01N 33/56911 (2013.01)

(58) Field of Classification Search
None
See application file for complete search history.

(56) References Cited

U.S. PATENT DOCUMENTS

| | | | |
|---|---|---|---|
| 6,075,150 A | 6/2000 | Wang et al. | |
| 2003/0064368 A1 | 4/2003 | Sakai et al. | |
| 2003/0119021 A1 | 6/2003 | Koster et al. | |
| 2007/0292442 A1 | 12/2007 | Wan et al. | |
| 2009/0170711 A1 | 7/2009 | Ellington et al. | |
| 2016/0106869 A1* | 4/2016 | Ghiani ............... | A61K 49/0054 424/9.6 |

FOREIGN PATENT DOCUMENTS

| | | |
|---|---|---|
| JP | 06-070765 A | 3/1994 |
| JP | 06-707065 A | 3/1994 |
| JP | 2002-501080 A | 1/2002 |
| JP | 2009-165475 A | 7/2009 |
| JP | 2009-192548 A | 8/2009 |
| JP | 2010-523157 A | 7/2010 |
| JP | 2014-218494 A | 11/2014 |
| JP | 2017-052753 A | 3/2017 |
| WO | WO-2016/128476 A1 | 8/2016 |
| WO | WO-2017/033966 A1 | 3/2017 |

OTHER PUBLICATIONS

Hirayama, Yuichiro et al., Chiba 2017 Lecture abstracts of the 64th annual conference of the Japanese Society of Society of Pharmacognosy) Aug. 25, 2017, p. 79 (Year: 2017).*
Zhang et al. Chem. Eur. vol. 21, pp. 19058-19063, 2015 (Year: 2015).*
Bian et al., "In Vivo Evidence for a Prodrug Activation Mechanism during Colibactin Maturation," ChemBioChem, 2013, 14:1194-1197.
Brotherton et al. "Isolation of a Metabolite from the pks Island Provides Insights into Colibactin Biosynthesis and Activity," Organic Letters, 2015, 17:1545-1548.
Eklof et al., "Cancer-associated fecal microbial markers in colorectal cancer detection," International Journal of Cancer, 2017, 141:2528-2536.
Hirayama et al., "Development of molecular probe to detect bacteria producing colorectal cancer risk factor colibactin," Symposium on Pharmacognosy, Sep. 9-10, 2017 (published Aug. 25, 2017), Chiba, Japan, Conference abstract 1C-11, with English translation.
International Preliminary Report on Patentability dated Dec. 10, 2019 in PCT/JP2018/031489, English translation.
International Search Report dated Nov. 27, 2018, in PCT/JP2018/031489, English translation.
Terentyeva et al., "Morpholinecarbonyl-Rhodamine 110 Based Substrates for the Determination of Protease Activity with Accurate Kinetic Parameters," Bioconjugate Chemistry, 2011, 22:1932-1938.

* cited by examiner

*Primary Examiner* — Jana A Hines
*Assistant Examiner* — Khatol S Shahnan Shah
(74) *Attorney, Agent, or Firm* — Foley & Lardner LLP

(57) ABSTRACT

The present invention provides a method and probe for determining colibactin and a colibactin-producing bacterium. According to the present invention, there is provided a fluorescent probe for detecting myristoyl asparagine using, for example, a tissue sample and a fecal sample and detecting enzyme activity of ClbP.

6 Claims, 7 Drawing Sheets
Specification includes a Sequence Listing.

Fig. 6

| No. | sex | age | portion | histology | subtype | depth | clb (tissue-derived DNA) tumor | clb (tissue-derived DNA) normal | Tumor tissue-derived bacterium Total number of colonies | Tumor tissue-derived bacterium clb-positive strain | Normal tissue-derived bacterium Total number of colonies | Normal tissue-derived bacterium clb-positive strain |
|---|---|---|---|---|---|---|---|---|---|---|---|---|
| 1 | F | 65 | C | adenocarcinoma | tub1>tub2 | SS | + | - | 22 | 8 | 0 | |
| 2 | M | 72 | Ra | adenocarcinoma | tub1>tub2 | MP | + | - | 9 | 0 | 0 | |
| 3 | M | 79 | A | adenocarcinoma | tub1>tub2 | SS | + | - | 49 | 23 | 56 | 0 |
| 4 | M | 70 | A | adenocarcinoma | tub1>tub2 | MP | - | - | 9 | 0 | 15 | 0 |
| 5 | M | 75 | S | adenocarcinoma | tub2 | SI | + | - | 0 | 0 | 0 | |
| 6 | F | 68 | A | adenocarcinoma | tub1>tub2 | SS | + | - | 6 | 0 | 5 | 0 |
| 7 | F | 75 | A | adenocarcinoma | tub2>>tub1 | MP | - | - | 14 | 0 | 0 | |
| 8 | M | 62 | S | adenocarcinoma | tub2>tub1 | SS | - | + | 1 | 0 | 11 | 0 |
| 9 | F | 73 | T | adenocarcinoma | muc>sig>>tub2 | SE | - | - | 18 | 4 | 1 | 0 |
| 10 | M | 82 | A | adenocarcinoma | tub1>tub2>muc | MP | + | - | 48 | 0 | 4 | 0 |
| 11 | M | 76 | A | adenocarcinoma | por1>tub2 | SS | + | - | 2 | 1 | 7 | 0 |
| 12 | F | 68 | D | adenocarcinoma | tub2 | SS | - | - | 10 | 0 | 4 | 1 |
| 13 | M | 71 | A | adenocarcinoma | tub1>tub2 | SS | - | - | 32 | 0 | 0 | |
| 14 | F | 62 | Ra | adenocarcinoma | tub2>tub1 | SS | + | - | | | | |
| | | | | | | | 8/14 (57.1%) | 1/14 (7.1%) | 220 | 36 (16.4%) | 103 | 1 (0.9%) |

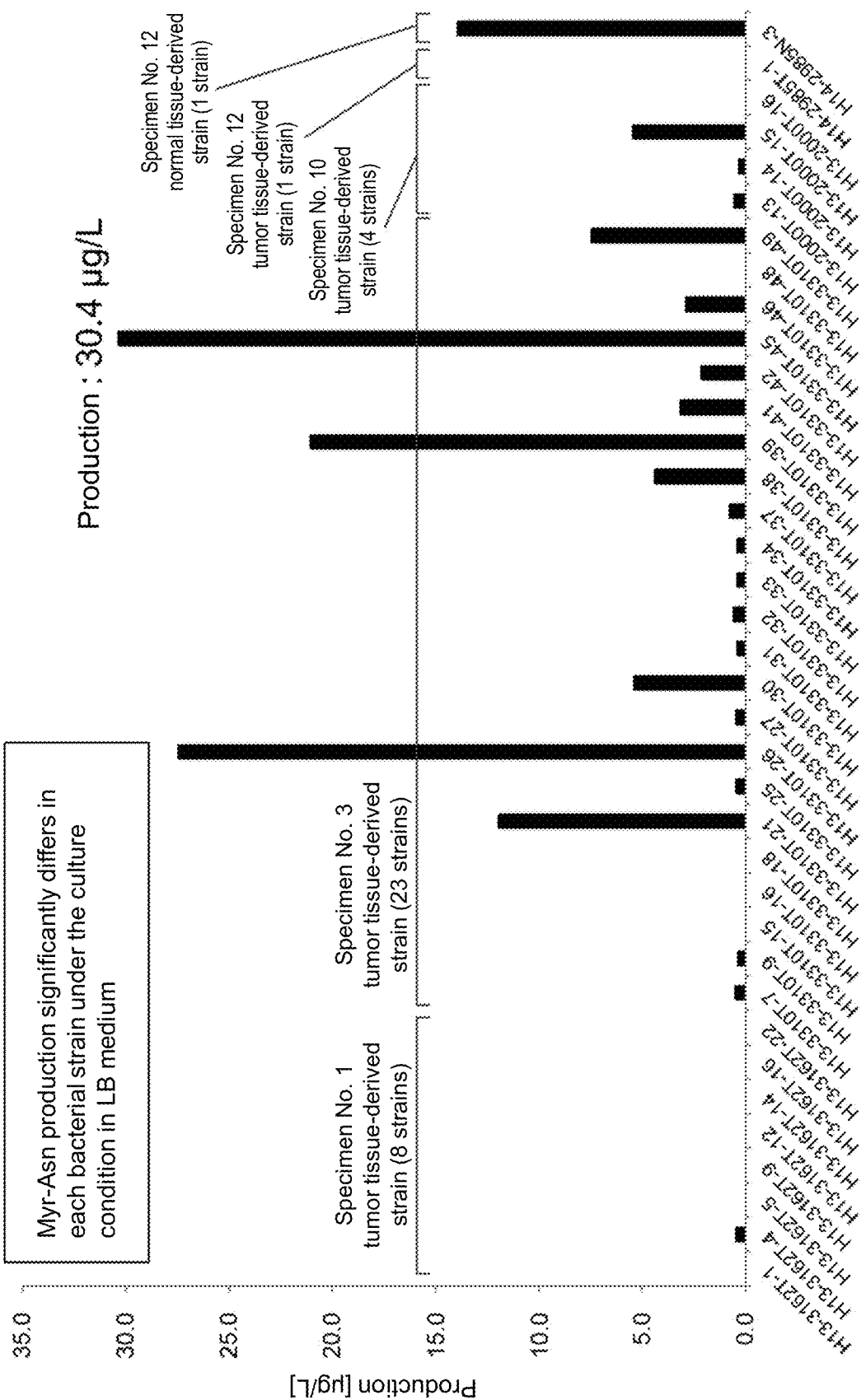

SEQUENCE LISTING

<160> NUMBER OF SEQ ID NOS: 8

<210> SEQ ID NO 1
<211> LENGTH: 27
<212> TYPE: DNA
<213> ORGANISM: Artificial Sequence
<220> FEATURE:
<223> OTHER INFORMATION: clbA forward primer

<400> SEQUENCE: 1
gttcaatatc gacaccaagc tcgcagt         27

<210> SEQ ID NO 2
<211> LENGTH: 32
<212> TYPE: DNA
<213> ORGANISM: Artificial Sequence
<220> FEATURE:
<223> OTHER INFORMATION: clbA reverse primer

<400> SEQUENCE: 2
acccgttatc tctgcgtgaa agacaagtat tg         32

<210> SEQ ID NO 3
<211> LENGTH: 25
<212> TYPE: DNA
<213> ORGANISM: Artificial Sequence
<220> FEATURE:
<223> OTHER INFORMATION: clbJ forward primer

<400> SEQUENCE: 3
tggcctgtat tgaaagagca ccgtt         25

<210> SEQ ID NO 4
<211> LENGTH: 25
<212> TYPE: DNA
<213> ORGANISM: Artificial Sequence
<220> FEATURE:
<223> OTHER INFORMATION: clbJ reverse primer

<400> SEQUENCE: 4
aatgggaacg gttgatgacg atgct         25

<210> SEQ ID NO 5
<211> LENGTH: 25
<212> TYPE: DNA
<213> ORGANISM: Artificial Sequence
<220> FEATURE:
<223> OTHER INFORMATION: clbQ forward primer

<400> SEQUENCE: 5
ctgtgtctta cgatggtgga tgccg         25

<210> SEQ ID NO 6
<211> LENGTH: 25
<212> TYPE: DNA
<213> ORGANISM: Artificial Sequence
<220> FEATURE:
<223> OTHER INFORMATION: clbQ reverse primer

<400> SEQUENCE: 6
gcattaccag attgtcagca tcgcc         25

<210> SEQ ID NO 7
<211> LENGTH: 25
<212> TYPE: DNA
<213> ORGANISM: Artificial Sequence

```
<220> FEATURE:
<223> OTHER INFORMATION: clbB forward primer

<400> SEQUENCE: 7
tgttccgttt tgtgtggttt cagcg                                                  25

<210> SEQ ID NO 8
<211> LENGTH: 25
<212> TYPE: DNA
<213> ORGANISM: Artificial Sequence
<220> FEATURE:
<223> OTHER INFORMATION: clbB reverse primer

<400> SEQUENCE: 8
gtgcgctgac cattgaagat ttccg                                                  25
```

DETECTION METHOD AND DETECTION PROBE FOR COLIBACTIN AND COLIBACTIN-PRODUCING BACTERIA

CROSS-REFERENCE TO RELATED APPLICATIONS

This application is the U.S. National Stage of PCT/JP2018/031489, filed Aug. 27, 2018, which claims priority to JP 2017-163079, filed Aug. 28, 2017.

The instant application contains a Sequence Listing which has been submitted in ASCII format via EFS-WEB and is hereby incorporated by reference in its entirety. Said ASCII copy, created on Feb. 24, 2020, is named sequence.txt and is 1,858 bytes.

TECHNICAL FIELD

The present invention relates to a detection method and a detection probe for colibactin and a colibactin-producing bacterium.

BACKGROUND ART

Colibactin is known as a causative factor for colorectal cancer, and produced in the intestine by a specific group of *Escherichia coli*. Colibactin is considered to have an activity to cleavage DNA in animal cells. It is reported that a colibactin-producing bacterium was detected in 67% of the colorectal cancer patients and 40% of the inflammatory bowel disease patients.

With respect to colibactin, the structure of myristoyl asparagine serving as a prodrug motif of colibactin and detection thereof by LC-MS have been reported (Non Patent Literature 1). Up to present, the chemical structure of colibactin has not been determined.

CITATION LIST

Non Patent Literature

Non Patent Literature 1: Brotherton C A et al., Org. Lett., Vol. 17, Page. 1545-1548 (2015)

SUMMARY OF INVENTION

The present invention provides a detection method and a detection probe for colibactin and a colibactin-producing bacterium.

The present inventors found that colibactin and a colibactin-producing bacterium can be detected in fecal samples (particularly, dried fecal samples) and colorectal cancer tissue samples by using a colibactin prodrug motif, i.e., myristoyl asparagine. The present inventors also succeeded in synthesizing a fluorescent probe for detecting a colibactin-producing bacterium. The present inventors also found that a colibactin producing enzyme, ClbP, can be detected in fecal samples (particularly dried fecal samples) and colorectal cancer tissues, by such a fluorescent probe. The present inventors also found that various types of fluorescent probes detecting ClbP can be designed based on the same principle. The present invention was attained based on these findings.

According to the present invention, for example, the following inventions are provided.

[1] A compound or a fluorescent probe selected from the group consisting of:

(A) a compound or a fluorescent probe obtained by connecting an amino group of a coumarin fluorescent dye having the amino group at position 7 of a coumarin skeleton and a carboxyl group of myristoyl asparagine via an amide bond;

(B) a compound or a fluorescent probe obtained by connecting an amino group of a naphthalimide fluorescent dye having the amino group at position 4 of a naphthalimide skeleton and a carboxyl group of myristoyl asparagine via an amide bond;

(C) a compound or a fluorescent probe obtained by connecting an amino group of naphthalene, pyrene or anthracene having the amino group at position 2 thereof and a carboxyl group of myristoyl asparagine via an amide bond;

(D) a compound or a fluorescent probe obtained by connecting one or both of amino groups of a rhodamine fluorescent dye having the amino group at position 3 and/or 9 of a xanthene skeleton and carboxyl group(s) of myristoyl asparagine via an amide bond;

(E) a compound or a fluorescent probe obtained by connecting one or both of amino groups of Bodipy fluorescent dye having the amino group at position 1 and/or 7 of Bodipy mother nucleus and the carboxyl group(s) of myristoyl asparagine via an amide bond;

(F) a compound or a fluorescent probe obtained by connecting said carboxyl group and said amino group in any one of (A) to (E) via alanine (—NH—CH(CH$_3$)—CO—) (each forms an amide bond with alanine);

(G) a compound or a fluorescent probe obtained by connecting a carboxyl group of myristoyl asparagine and a hydroxyl group of oFlu, which is a fluorescent group that exhibits fluorescence when the hydroxyl group is released, via a self-cleavable linker, wherein the self-cleavable linker is connected to the carboxyl group of myristoyl asparagine via an amide bond; and the hydroxyl group of oFlu is liberated when the amide bond is decomposed by hydrolysis; and (H) a compound or fluorescent probe having a fluorescent dye connected to a carboxyl group of myristoyl asparagine via an amide bond, wherein fluorescence is emitted after the amide bond is cleaved in a ClbP dependent manner.

[2] The compound or the fluorescent probe according to [1], wherein the compound or the fluorescent probe is (A) a compound or a fluorescent probe obtained by connecting an amino group of a coumarin fluorescent dye having the amino group at position 7 of a coumarin skeleton and a carboxyl group of myristoyl asparagine via an amide bond.

[3] The compound or the fluorescent probe according to [1], wherein the compound or the fluorescent probe is (B) a compound or a fluorescent probe obtained by connecting an amino group of a naphthalimide fluorescent dye having the amino group at position 4 of a naphthalimide skeleton and a carboxyl group of myristoyl asparagine via an amide bond.

[4] The compound or the fluorescent probe according to [1], wherein the compound or the fluorescent probe is (C) a compound or a fluorescent probe obtained by connecting an amino group of naphthalene, pyrene or anthracene having the amino group at position 2 thereof and a carboxyl group of myristoyl asparagine via an amide bond.

[5] The compound or the fluorescent probe according to [1], wherein the compound or the fluorescent probe is (D) a compound or a fluorescent probe obtained by connecting one or both of amino groups of a rhodamine fluorescent dye having the amino group at position 3 and/or 9 of a xanthene skeleton and carboxyl group(s) of myristoyl asparagine via an amide bond.

[6] The compound or the fluorescent probe according to [1], wherein the compound or the fluorescent probe is (E) a compound or a fluorescent probe obtained by connecting one or both of amino groups of Bodipy fluorescent dye having the amino group at position 1 and/or 7 of Bodipy mother nucleus and the carboxyl group(s) of myristoyl asparagine via an amide bond.

[7] A composition comprising the compound or the fluorescent probe according to any one of [1] to [6], for use in detecting a colibactin producing microorganism, for use in detecting a microorganism having a colibactin biosynthetic gene cluster and/or for use in detecting colibactin.

[8] The composition according to [7], for use in a tissue sample or fecal sample.

[9] The composition according to [8], wherein the tissue sample or fecal sample is a human tissue sample or fecal sample.

[10] A method for detecting the presence of colibactin or colibactin-producing *Escherichia coli* in a biological sample, comprising
detecting the presence or absence of myristoyl asparagine in the biological sample.

[11] The method according to [10], wherein the biological sample is a tissue sample or fecal sample.

[12] The method described in [10] or [11], wherein the biological sample is derived from a human.

BRIEF DESCRIPTION OF DRAWINGS

FIG. 6 shows detection of a colibactin biosynthetic gene using frozen samples of human colorectal cancer tissue and normal colorectal tissue of the same patients; and the percentages of colibactin biosynthetic gene-positive bacterium in the bacteria obtained by culturing homogenates of the tissue samples.

FIG. 7 shows the detection results of myristoyl-D-asparagine in cultures obtained by culturing bacteria.

DESCRIPTION OF EMBODIMENTS

Figure 1:
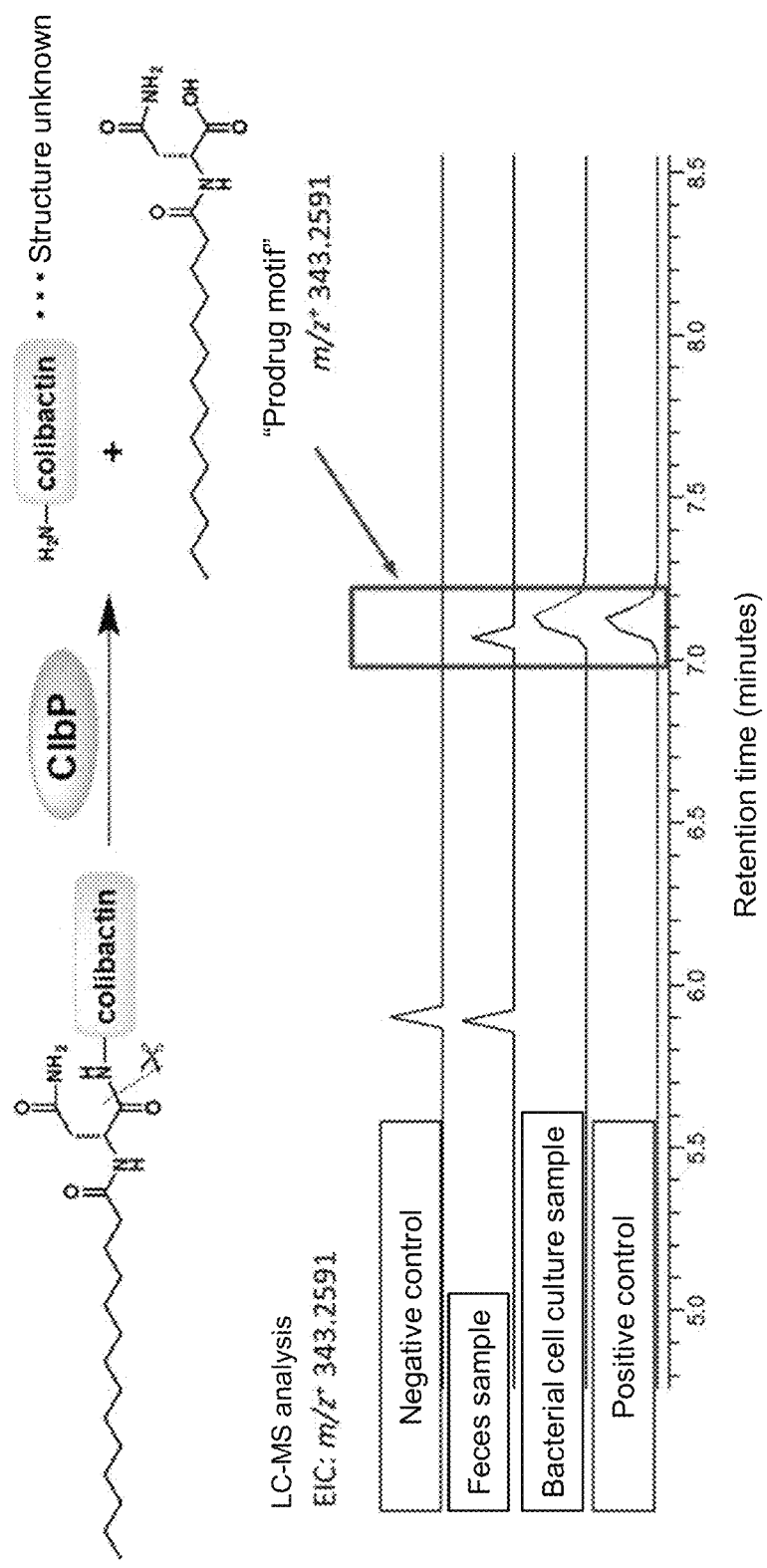
FIG. 1 is a chromatogram (obtained by liquid chromatography) showing that myristoyl asparagine separated from colibactin when colibactin is produced from a colibactin prodrug was detected in a dry fecal sample.

"Colibactin" is known as a molecule involved in onset of colorectal cancer and a low-molecular compound produced by a specific type of *Escherichia coli* of *E. coli* bacteria living in the intestine, which is clarified by biochemical analysis. However, the detailed chemical structure of colibactin is not known. Colibactin is synthesized as a prodrug inactive within the bacterial cell of *Escherichia coli*. In the periplasm of *Escherichia coli*, a prodrug motif (of colibactin) is removed by intramolecular cleavage to produce colibactin outside the bacterial cell of *Escherichia coli*.

The "colibactin-producing bacterium" refers to a bacterium producing colibactin. A specific group of *Escherichia coli* is known to produce colibactin in the intestine; however, not all mammals (particularly, human) have colibactin-producing bacteria. The colibactin-producing bacteria are known to have a colibactin polyketide synthesis gene cluster on the genome. The colibactin polyketide synthesis gene cluster encodes proteins involved in a colibactin biosynthetic pathway.

In the specification, the "ClbP" refers to one of the genes present in the colibactin polyketide synthesis gene cluster (for example, GenBank accession No.: AM229678.1). ClbP (gene) encodes, for example, a protein registered at GenBank: CAJ76284.1. The protein encoded by ClbP has a peptidase-like ability and cleaves a peptide bond (amide bond) connecting colibactin and myristoyl asparagine of a colibactin prodrug as a subject molecule. ClbP is expressed in the periplasm of *Escherichia coli* and conceivably converts the colibactin prodrug to colibactin in the periplasm.

In the specification, "emitting fluorescence in a ClbP dependent manner" means that when hydrolysis occurs within the molecule by the protein encoded by the ClbP (gene), the molecule obtains an ability to emit fluorescence. In the specification, "obtain an ability to emit fluorescence" means becoming to emit fluorescence having a specific wavelength with excitation light having a specific wavelength. For example, the phrase "obtain an ability to emit fluorescence" means that a molecule, which does not emit fluorescence or emit fluorescence of which intensity is no more than a detection threshold by excitation light with a specific wavelength, changes to emit fluorescence whose intensity is no less than the detection threshold.

In the specification, the "subject" refers to a warm-blooded animal and can be a bird or a mammal. Examples of the mammal include primates such as monkey, chimpanzee, gorilla, orangutan, bonobo and human; livestock animals such as pig, cow, horse, goat, and sheep; and pets such as dog and cat. Examples of the bird include chicken. In the specification, if a subject is expressed in terms of a "patient" or "body", the "patient" or "body" is a term for a human and a non-human warm-blooded animal. In the specification, the subject can be preferably a healthy body, a patient with an inflammatory bowel disease, a patient suspected to have an inflammatory bowel disease, a patient with a colorectal cancer or a patient suspected to have colorectal cancer.

In the specification, the "fecal sample" refers to a sample comprising feces discharged from a subject. The fecal sample is a sample ordinarily discharged through the anus.

The fecal sample may be a dried or lyophilized fecal sample. The fecal sample may be ground (for example, powder).

In the specification, the "fluorescent dye" refers to a chemical substance, which can be excited by (excitation) light having a specific wavelength and emits light (fluorescence) having a different specific wavelength. In the specification, "fluorescent probe" refers to a compound emitting fluorescence having a specific wavelength or a compound emitting fluorescence enhanced in intensity in a specific condition. In the specification, a compound which is cleaved in a ClbP dependent manner and emits fluorescence is referred to as a fluorescent probe.

Myristoyl asparagine has the following structure.

[Formula 1]

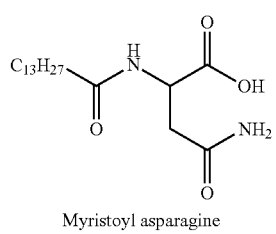

Myristoyl asparagine

Accordingly, myristoyl asparagine has a structure obtained by connecting a carboxyl group of myristic acid and an amino group of asparagine via an amide bond.

A colibactin prodrug has a structure obtained by connecting colibactin and myristoyl asparagine (prodrug motif) via an amide bond.

[Formula 2]

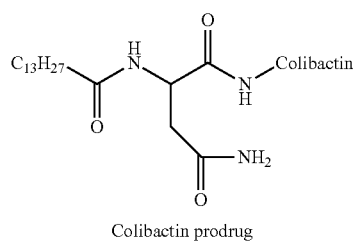

Colibactin prodrug

A coumarin fluorescent dye has the following basic skeleton (hereinafter referred to also as a "coumarin skeleton").

[Formula 3]

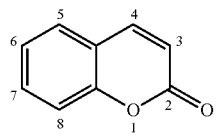

The above compound does not virtually emit fluorescence as it is. However, if an electron donating group is introduced in the position-7 of the coumarin skeleton, the compound exhibits strong light absorption characteristics, and becomes to emit fluorescence. If an electron donating group having a high electron donating ability is introduced into the position-7 of the compound in accordance with the aforementioned principle, a fluorescent dye emitting intensive fluorescence can be obtained.

In the present invention, myristoyl asparagine can be connected to the electron donating group (amino group) at the position-7 so as to lower the electron donating ability thereof. For example, if the electron donating group (amino group) at position 7 and a carboxyl group of myristoyl asparagine are connected via an amide bond, the electron donating ability of the electron donating group of a coumarin fluorescent dye at position 7 can be lowered. In contrast, in the present invention, a compound obtained by connecting a carboxyl group of myristoyl asparagine to a compound via an amide bond is recognized by the enzyme encoded by ClbP and can be cleaved at the amide bond into myristoyl asparagine and the original compound.

According to the present invention, a compound obtained by connecting a carboxyl group of myristoyl asparagine and the amino group at position 7 of a coumarin skeleton of a coumarin fluorescent dye via an amide bond can be recognized by the enzyme encoded by ClbP to emit fluorescence in a ClbP dependent manner. Accordingly, such a compound can be used for detecting the enzyme encoded by ClbP, a colibactin biosynthetic gene cluster, a Colibactin-producing *Escherichia coli* and/or colibactin.

In the present invention, there is provided a compound obtained by connecting an amino group of a compound having the amino group at position 7 of a coumarin skeleton of a coumarin fluorescent dye and a carboxyl group of myristoyl asparagine via an amide bond, and a fluorescent probe comprising the compound. The coumarin skeleton may have a methyl group that may be substituted (for example, —CH₃, —CN, —CH₂OH, methyl group substituted with 1 to 3 halogen atoms such as —CF₃ and —CH₂Br) at position 4. As examples of such compounds, the following compounds are mentioned.

Probe 1A

[Formula 4]

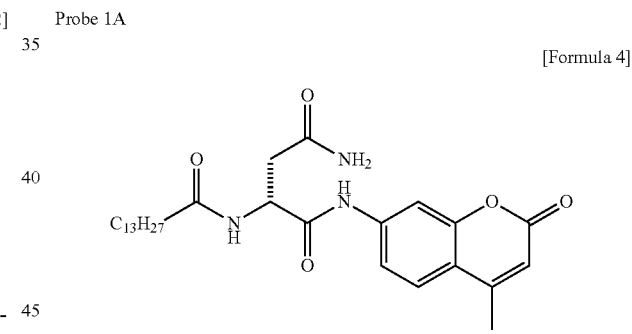

Probe 1B

[Formula 5]

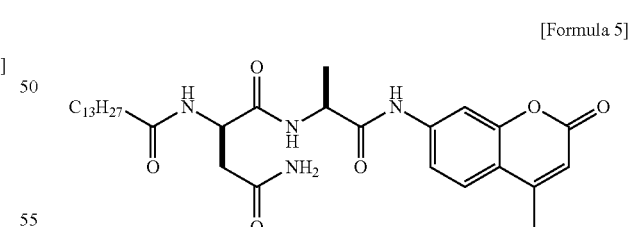

Probe 1C

[Formula 6]

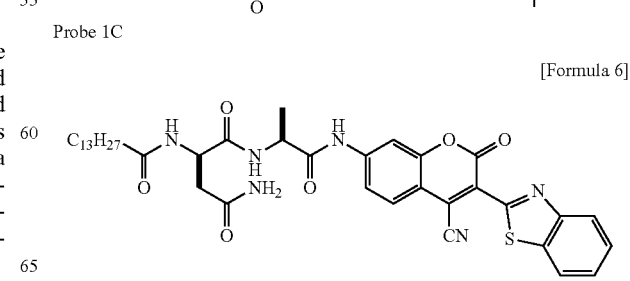

A naphthalimide fluorescent dye can be used similarly for designing a compound or probe, which emits fluorescence in a ClbP dependent manner.

[Formula 7]

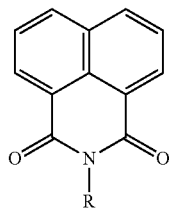

Naphthalimide skeleton

In the naphthalimide skeleton, R may be, for example, a $C_{1-6}$ alkyl that may be substituted, a $C_{1-6}$ alkenyl that may be substituted, or a $C_{1-6}$ alkynyl that may be substituted, but R is not limited to these.

A compound obtained by connecting an amino group of the naphthalimide fluorescent dye having the amino group at position 4 of its naphthalene ring and a carboxyl group of myristoyl asparagine via an amide bond is cleaved at the amide bond in a ClbP dependent manner to produce a naphthalimide fluorescent dye. As such a naphthalimide-based probe, the following compound is mentioned.

Probe 2

[Formula 8]

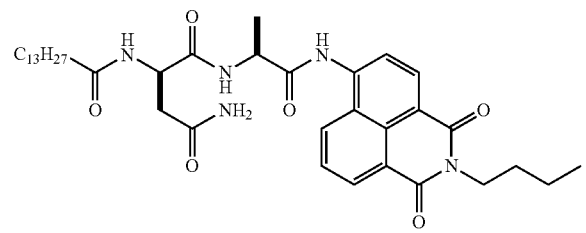

Similarly, if naphthalene substituted with an amino group, pyrene substituted with an amino group and anthracene substituted with an amino group each are used to form a compound by connecting a carboxyl group of myristoyl asparagine and the amino group via the amide bond, the compound can be used as a probe emitting fluorescence by cleaving the amide bond moiety in a ClbP dependent manner. Naphthalene, pyrene and anthracene each preferably have an amino group at position 2 which can form an amide bond. As an example of such compounds, for example, the following compound is mentioned.

Probe 3

[Formula 9]

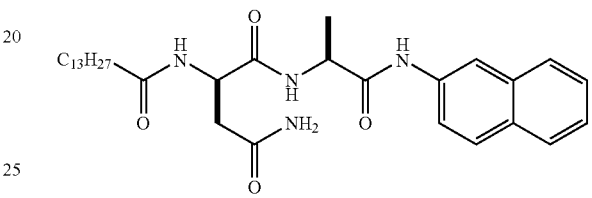

If a rhodamine fluorescent dye has an electron donating group (for example, amino group) at position 3 and position-9 of the xanthene skeleton thereof, the rhodamine fluorescent dye emits intensive fluorescence. If the electron donating ability of these electron donating groups is reduced, intensity of fluorescence can be reduced. Accordingly, if a compound is obtained by connecting either one or all of the amino groups of the rhodamine fluorescent dye having an amino group at position 3 and/or position-9 of the xanthene skeleton and a carboxyl group of myristoyl asparagine via an amide bond, the compound can be used as a probe emitting fluorescence by cleaving the amide bond moiety in a ClbP dependent manner. For example, a compound obtained by connecting each of the amino acids of a rhodamine fluorescent dye having an amino acid at position 3 and position-9 of the xanthene skeleton and a carboxyl group of myristoyl asparagine via an amide bond can be provided. As an example of such a compound, the following compound is mentioned.

Probe 4

[Formula 10]

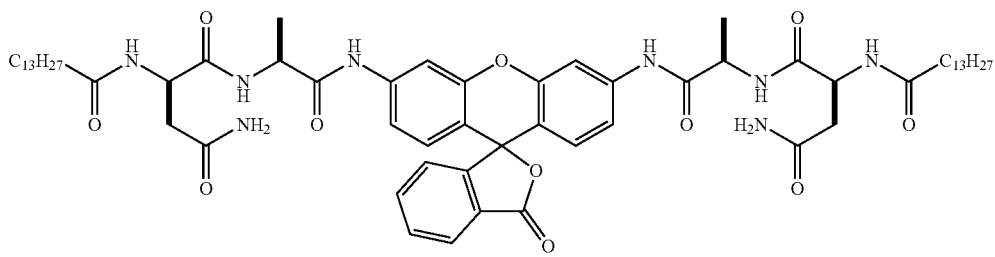

The same applies to a Bodipy fluorescent dye. Bodipy has the following Bodipy mother nucleus structure: (4,4-difluoro-4-bora-3a,4a-diaza-s-indacene).

[Formula 11]

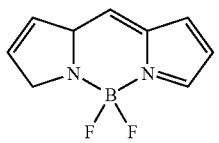

A compound obtained by connecting an amino acid(s) of a Bodipy fluorescent dye having the amino acid at position 1 and/or 7 of the mother nucleus and a carboxyl group of myristoyl asparagine via an amide bond can be used as a probe emitting fluorescence by cleaving the amide bond in a ClbP dependent manner. As such a compound, for example, a compound having the following structure is mentioned.

Probe 5

[Formula 12]

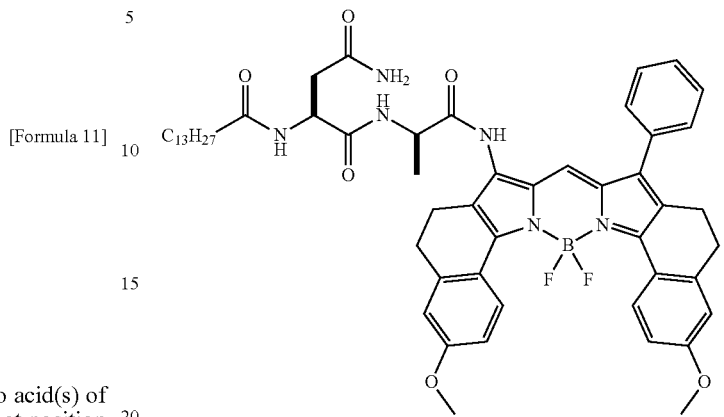

Other compounds having the following structures can be used as probes emitting fluorescence by cleaving the amide bond in a ClbP dependent manner. As such compounds, for example, compounds having the following structures are mentioned.

Probe 6

[Formula 13]

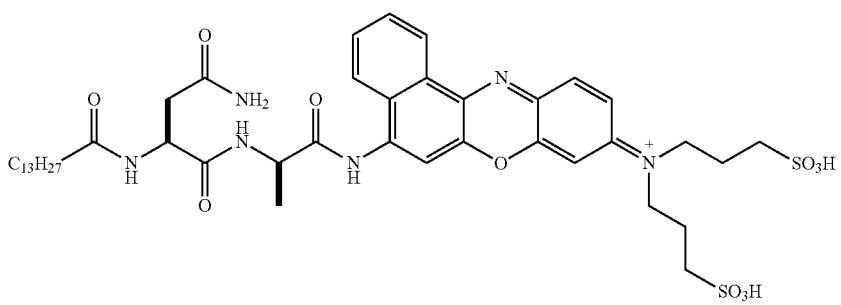

Probe 7

[Formula 14]

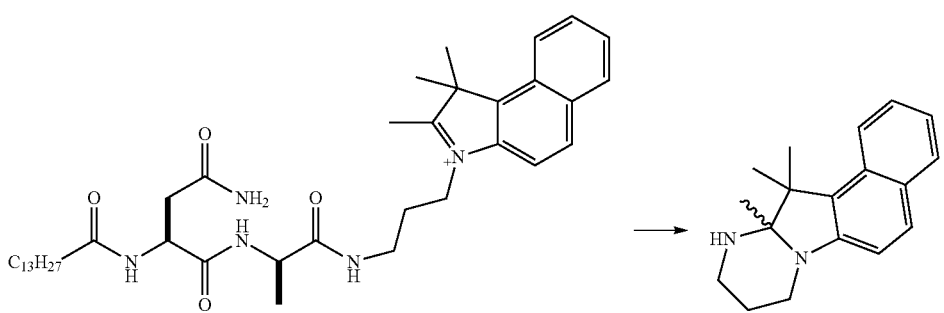

Probe 8

[Formula 15]

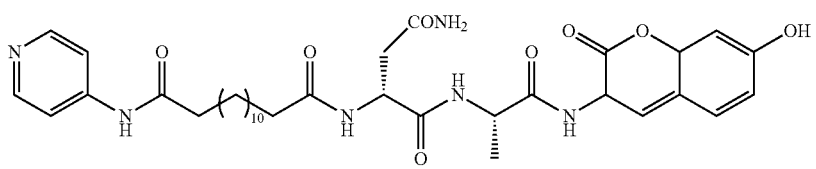

Note that, in probe 8, emission of fluorescence from a coumarin skeleton is inhibited by PET at a pyridine ring within the molecule; however, probe 8 is designed such that a coumarin fluorescent dye is liberated by cleavage with ClbP to emit fluorescence.

A dye having a phenolic fluorescent group (oFlu) such as TokyoGreen, which emits fluorescence by liberating a hydroxyl group, can be used as a probe emitting fluorescence by cleaving the amide bond in a ClbP dependent manner. As such a compound, for example, the following compounds are mentioned.

Probe 9A

[Formula 16]

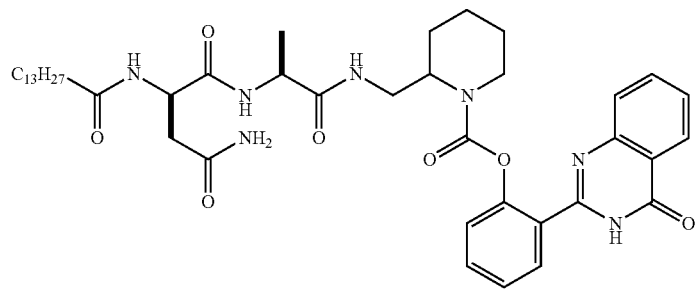

Probe 9B

[Formula 17]

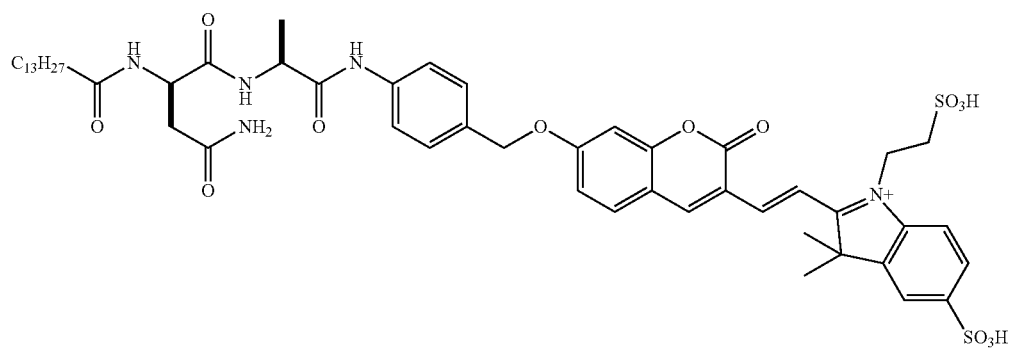

As a self-cleavable linker (linker connecting a fluorescent dye moiety and a myristoyl asparagine moiety), for example, the following linkers can be used. In the following formula, the structures of linkers are shown on the left side, and mechanisms of how to cleave the corresponding linkers are shown on the right side.

Self-cleavable linkers

[Formula 18]

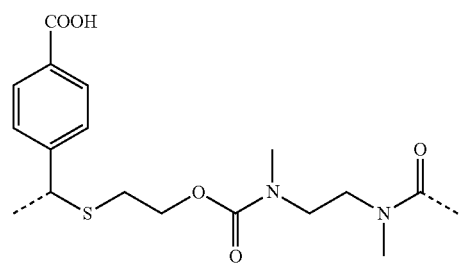

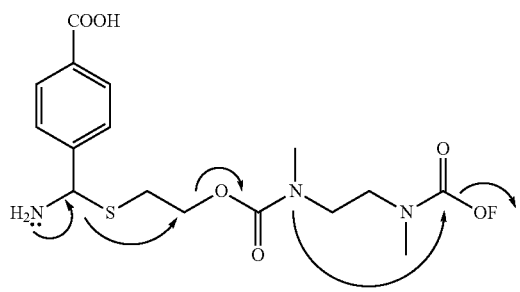

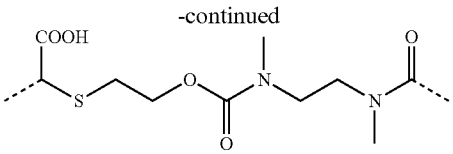

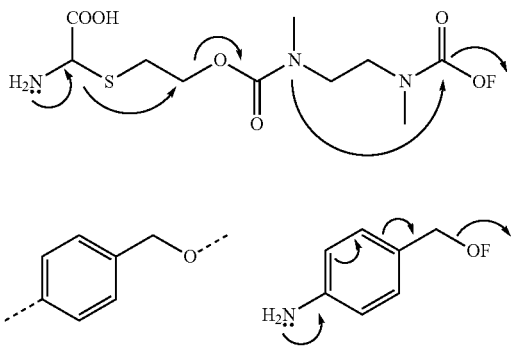

-continued

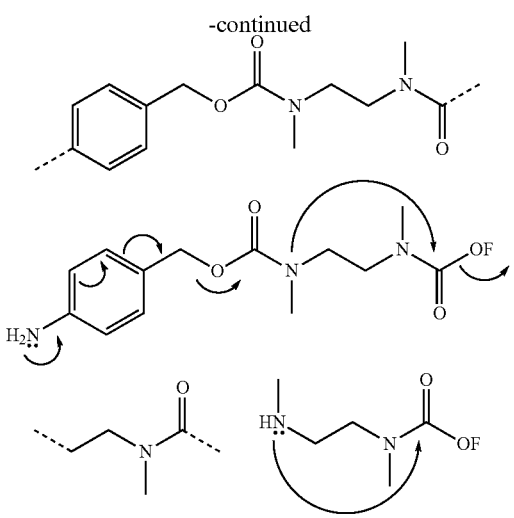

The compound, which is obtained by connecting myristoyl asparagine and oFlu via any one of the aforementioned linkers, can be used as a probe emitting fluorescence by cleaving at the amide moiety in a ClbP dependent manner. In the same mechanism, a compound, which is obtained by connecting the hydroxyl group such as, e.g. oFlu of a compound, which is selected from TokyoGreen, TokyoMagenta, Oregon green, SNAFL, carboxyfluorescein, carboxyfluorescein diacetate, fluorescein, and fluorescein isocyanate (FITC), and a compound having a hydroxyl group which is used as a group to be connected to a carboxyl group of myristoyl asparagine in place of the amino group, and a carboxyl group of myristoyl asparagine by an amide bond via a self-cleavable linker, can be used as a probe emitting fluorescence by cleaving the amide bond moiety in a ClbP dependent manner.

In the present invention, a fluorescence compound or a fluorescent probe may be present in the form of a salt and/or a solvate. Not only a free compound but also a salt and/or a solvate thereof are included in the compounds and probes specified by, e.g., the above chemical formulas. Solvents comprised in solvates may include water and ethanol. The solvate comprising water as a solvent is called a hydrate.

In the above, if myristoyl asparagine is connected to a fluorescent dye via alanine (—NH—CH(CH$_3$)—CO—), alanine may be deleted. In the above, myristoyl asparagine is directly connected to a fluorescent dye without alanine, myristoyl asparagine may be connected to the fluorescent dye via alanine. This is because the cleaving activity of an enzyme encoded by ClbP gene allows intermediation of alanine. Note that, an amide bond can be formed between alanine and a carboxyl group of myristoyl asparagine and an amide bond is formed between alanine and an amino group of a fluorescent dye. In this manner, myristoyl asparagine and the fluorescent dye can be connected.

According to the present invention, there is provided a fluorescent probe comprising a compound as mentioned above. According to the present invention, there is provided a composition comprising a compound or a fluorescent probe as mentioned above for use in detecting a colibactin producing microorganism, a microorganism having a colibactin biosynthetic gene cluster and/or colibactin. These compositions may be used for detecting a colibactin producing microorganism, a microorganism comprising a colibactin biosynthetic gene cluster and/or colibactin (or probability of the presence of colibactin is checked) in a fecal sample.

The probe of the present invention is cleaved and emits fluorescence in the presence of an enzyme encoded by ClbP gene. The probe of the present invention can be used for evaluating the presence or absence of the enzyme encoded by ClbP gene or a colibactin positive bacterium in a sample exposed to the probe, based on the intensity of the fluorescence as an index. In one aspect, the fluorescence intensity of a test sample may be evaluated in comparison with the fluorescence intensity exhibited by the probe of the present invention with the samples obtained from a patient group, in which a colibactin positive bacterium has been detected, and/or the fluorescence intensity exhibited by the probe of the present invention with the samples obtained from a patient group in which a colibactin positive bacterium has not been detected. For example, if the fluorescence intensity of a test sample is higher than the average value, third quartile value or first quartile value of the fluorescence intensity exhibited by a probe of the present invention with the samples of a patient group in which a colibactin positive bacterium has been detected, it may be evaluated that the test sample comprises a colibactin positive bacterium. In contrast, for example, if the fluorescence intensity of a test sample is lower than the first quartile value of the fluorescence intensity exhibited by a probe of the present invention with the samples of a patient group in which a colibactin positive bacterium has been detected, it may be evaluated that the test sample does not comprise a colibactin positive bacterium. Alternatively, for example, if the fluorescence intensity of a test sample is lower than the average value, third quartile value or first quartile value of the fluorescence intensity exhibited by a probe of the present invention with the samples of a patient group in which a colibactin positive bacterium has not been detected, it may be evaluated that the test sample does not comprise a colibactin positive bacterium. In addition, for example, if the fluorescence intensity of a test sample is higher than the third quartile value of the fluorescence intensity exhibited by a probe of the present invention with the samples of a patient group in which a colibactin positive bacterium has not been detected, it may be evaluated that the test sample comprises a colibactin positive bacterium.

In this sense, the threshold may be a value between a maximum value of the fluorescence intensity exhibited by a probe of the present invention with the samples of a patient group in which a colibactin positive bacterium has been detected and a third quartile value thereof; a value between the maximum value and an average value thereof; a value between the maximum value and a first quartile value thereof; a value between the average value and the third quartile value; a value between the average value and the first quartile value; or a value between the third quartile value and the first quartile value. Alternatively, the threshold may be a value between a value selected from the group consisting of a maximum value, first quartile value, average value and third quartile value of the fluorescence intensity, which is exhibited by a probe of the present invention with the samples of a patient group in which a colibactin positive bacterium has been detected, and a maximum value or third quartile value of the fluorescence intensity, which is exhibited by a probe of the present invention with the samples of a patient group in which a colibactin positive bacterium has not been detected. In this case, if the fluorescence intensity exhibited by a probe of the present invention with a test sample is higher than the threshold, it can be evaluated that a colibactin positive bacterium is comprised in the test sample or the probability of comprising the bacterium is high; and/or, if the fluorescence intensity exhibited by a probe of the present invention with a test sample is lower than the threshold, it can be evaluated that a colibactin positive bacterium is not comprised in the test sample or the probability of not-comprising the bacterium is high.

The threshold may be a value between a maximum value of the fluorescence intensity exhibited by a probe of the present invention with the samples of a patient group in which a colibactin positive bacterium has not been detected, and a third quartile value thereof; a value between the maximum value and an average value thereof; a value between the maximum value and a first quartile value thereof; a value between the average value and the third quartile value; or a value between the third quartile value and the first quartile value. Alternatively, the threshold may be a value between a value selected from the group consisting of a maximum value, first quartile value, average value and third quartile value of the fluorescence intensity exhibited by a probe of the present invention with samples obtained from a patient group in which a colibactin positive bacterium has not been detected and the minimum value or the first quartile value of the fluorescence intensity exhibited by the probe of the present invention with samples obtained from a patient group in which a colibactin positive bacterium has been detected. If the fluorescence intensity exhibited by the probe with the test sample measured is higher than the threshold, it can be evaluated that a colibactin positive bacterium is comprised in the test sample or the probability of comprising the bacterium is high; and/or, if the fluorescence exhibited by the probe with a test sample is lower than the threshold, it can be evaluated that a colibactin positive bacterium is not comprised in the test sample or the probability of not-comprising the bacterium is high.

Alternatively, the threshold can be the maximum value of the fluorescence intensity exhibited by a probe of the present invention with samples obtained from a patient group in which a colibactin positive bacterium has not been detected. If the fluorescence intensity exhibited by a probe of the present invention with a test sample (measured) is higher than the threshold, it can be evaluated that a colibactin positive bacterium is comprised in the test sample or the probability of comprising the bacterium is high; whereas the fluorescence intensity exhibited by a probe of the present invention with a test sample is lower than the threshold, it can be evaluated that a colibactin positive bacterium is not comprised in the test sample or the probability of not-comprising the bacterium is high Alternatively, the threshold can be the lowest value of the fluorescence intensity exhibited by a probe of the present invention with samples obtained from a patient group in which a colibactin positive bacterium has been detected. In this case, if the fluorescence intensity exhibited by a probe of the present invention with a test sample (measured) is higher than the threshold, it can be evaluated that a colibactin positive bacterium is comprised in the test sample or the probability of comprising the bacterium is high; and/or, if the fluorescence intensity exhibited by a probe of the present invention with a test sample is lower than the threshold, it can be evaluated that a colibactin positive bacterium is not comprised in the test sample or the probability of not-comprising the bacterium is high.

Alternatively, the threshold may be a value between the lowest value of the fluorescence intensity exhibited by a probe of the present invention with samples obtained from a patient group in which a colibactin positive bacterium has been detected and the maximum value of the fluorescence intensity exhibited by a probe of the present invention with samples obtained from a patient group in which a colibactin positive bacterium has not been detected. In this case, if the fluorescence intensity exhibited by a probe of the present invention with a test sample (measured) is higher than the threshold, it can be evaluated that a colibactin positive bacterium is comprised in the test sample or the probability of comprising the bacterium is high; and/or, if the fluorescence intensity exhibited by a probe of the present invention with a test sample is lower than the threshold, it can be evaluated that a colibactin positive bacterium is not comprised in the test sample or the probability of not-comprising the bacterium is high.

The patient group in which a colibactin positive bacterium has been detected and the patient group in which a colibactin positive bacterium has not been detected, can be previously determined based on whether or not a colibactin biosynthetic gene is detected in a sample and whether or not myristoyl-D-asparagine is detected in a sample.

Those skilled in the art can understand that if the threshold for use in the aforementioned determination is set higher, a false positive rate will decrease but a false negative rate will increase; and if the threshold is set lower, a false positive rate will increase but the false negative rate will decrease. Likewise, the threshold can be set depending on the purpose.

According to the present invention, there is provided a method for predicting the presence of colibactin or a colibactin-producing *Escherichia coli* in a biological sample, comprising detecting the presence or absence of myristoyl asparagine in the biological sample.

In one aspect of the method of the present invention, the biological sample is a fecal sample, for example, a human fecal sample. In one aspect of the method of the present invention, the biological sample is a tissue sample comprising a cancer tissue or comprising a tissue suspected as cancer, for example, a human tissue sample {the tissue sample herein may be a frozen sample}. Myristoyl asparagine detected means that colibactin in an active form is produced from a prodrug in a non-active form. Accordingly, myristoyl asparagine detected in a biological sample means that colibactin is comprised in the biological sample. The fact that colibactin is comprised in the biological sample shows that a colibactin-producing bacterium (for example, *Escherichia coli*) is present in the feces sample. That is to say, the fact that myristoyl asparagine has been detected in a fecal sample by the method of the present invention indicates that colibactin and/or colibactin-producing bacterium (for example, *Escherichia coli*) is present in the large bowel of a subject (e.g., human) from which the fecal (biological) sample is derived. Since colibactin is known as a pathogenesis of colorectal cancer, the method of the present invention can be used in determining whether or not a subject (for example, human) has a predisposing factor of colorectal cancer. The method of the present invention may be a method comprising no medical actions by a physician's to a human body (i.e., industrial applicable method).

According to one aspect of the present invention, a fecal sample may be cultured in the conditions suitable for proliferation of *Escherichia coli*, and thereafter, subjected to analysis. According to the present inventors, the amount of colibactin-producing *Escherichia coli* increased by culturing it, the detection sensitivity for colibactin and a colibactin-producing bacterium was improved. In the present invention, it is not essential to isolate a colibactin positive bacterium.

According to the present invention, there is provided a method for predicting the presence of colibactin or colibactin-producing *Escherichia coli* in a biological sample, comprising detecting the presence or absence of the enzymatic activity of an enzyme encoded by ClbP in the biological sample.

The presence or absence of the enzymatic activity of an enzyme encoded by ClbP can be determined by use of a fluorescent compound or a fluorescent probe which is cleaved in a ClbP dependent manner to emit fluorescence.

According to the present invention, the activity of the enzyme encoded by ClbP was successfully detected by use of a fecal sample (particularly, dried fecal sample). Thus, according to the present invention, the biological sample may be a fecal sample or a dried fecal sample.

EXAMPLES

Example 1: Detection of Colibactin

In the Example, detection of colibactin from biological samples was tried.

Specifically, colibactin is a chemical substance unknown in structure. It is known that colibactin is from a prodrug produced inside a bacterial cell of *Escherichia coli* having a colibactin production system. This colibactin prodrug is cleaved into myristoyl asparagine (prodrug motif) and colibactin by an enzyme on the intima in the periplasm of *Escherichia coli* to produce active colibactin. In this Example, detection of the prodrug motif in biological samples was carried out as a trial.

In the Example, human feces samples (23 cases) were taken from volunteers each having no pathological lesion observed in the large bowel and used as biological samples. At first, *Escherichia coli* genomic DNA was extracted from fecal samples and purified. Thereafter, in order to check whether *Escherichia coli* having a colibactin production system is present or not, clbA gene, clbJ gene and clbQ gene in the colibactin biosynthetic gene cluster were amplified by PCR and the presence or absence of them were checked.

The primers used for amplification of individual genes are as follows:

```
clbA forward primer
                                    (SEQ ID NO: 1)
GTTCAATATCGACACCAAGCTCGCAGT clbA reverse primer
                                    (SEQ ID NO: 2)
ACCCGTTATCTCTGCGTGAAAGACAAGTATTG clbJ forward primer
                                    (SEQ ID NO: 3)
TGGCCTGTATTGAAAGAGCACCGTT clbJ reverse primer
                                    (SEQ ID NO: 4)
AATGGGAACGGTTGATGACGATGCT clbQ forward primer
                                    (SEQ ID NO: 5)
CTGTGTCTTACGATGGTGGATGCCG clbQ reverse primer
                                    (SEQ ID NO: 6)
GCATTACCAGATTGTCAGCATCGCC
```

In 2 cases out of the 23 cases, amplification of clbA gene, clbJ gene and clbQ gene was confirmed. It was demonstrated that *Escherichia coli* having a colibactin biosynthetic gene cluster is present in feces.

In one of the cases, a prodrug motif was extracted from feces, purified and subjected to LC-MS by the following procedure. To describe it specifically, dry feces (about 40 mg) was suspended in milliQ water. Subsequently, 800 μL of ethyl acetate was added to the suspension, stirred and centrifuged at 4° C. for 10 minutes. The resultant ethyl acetate layer was recovered and centrifugally concentrated. The precipitate was dissolved in 50 μL of DMF and centrifuged. The supernatant was subjected to LC-MS analysis (Q Exactive). When a bacterial cell sample was used, *Escherichia coli* was cultured in 10 mL of LB medium at 37° C. for 24 hours with shaking, added 10 mL of ethyl acetate, stirred and centrifuged, and the resultant ethyl acetate layer was recovered and centrifugally concentrated. The precipitate was dissolved in 50 μL of DMF and centrifuged. The supernatant was subjected to LC-MS analysis (Q Exactive).

LC-MS conditions were as follows.
Column Conditions:
ACQUITY UPLC HSS C18 Column
2.1×50 mm Column
Solvent Conditions:
A: H2O/MeCN=95/5 (0.05% FA)
B: MeCN (0.05% FA)
HPLC Conditions:
(1) B 10%→50% gradient (0 to 5 min)
(2) B 50% isocratic (5 to 7.5 min)
(3) A 100% (7.5 toll min)

*Escherichia coli* DH5α was used as a negative control and Nissle 1917 was used as a positive control. As a bacterial cell culture sample, *Escherichia coli* isolated by the present inventors and confirmed to encode a colibactin biosynthetic gene, was used. The results were as shown in FIG. 1.

As shown in FIG. 1, in the chromatograph of a feces sample of the above patient, a peak exhibiting the same mass-to-charge ratio (m/z+ 343.2591) as that intrinsic to a prodrug motif was detected at a time point indicating the same retention time as in the positive control and the bacterial cell culture sample. From the result, it became apparent that the colibactin prodrug motif can be directly detected from a fecal sample. Since the prodrug motif is intrinsic to colibactin, detection of a prodrug motif in a fecal sample means that colibactin (active type) unknown in structure is present in the fecal sample. In the Example, it was clear that the presence of colibactin can be detected by detecting the prodrug motif in a fecal sample.

Example 2: Design of Probe for Detecting *Escherichia coli* Having Colibactin Production System In the Example, a probe that can detect *Escherichia coli* having a colibactin production system was designed.

A compound (probe 1) having a structure in which a carboxyl group of myristoyl asparagine and the amino acid of aminomethyl coumarin (AMC) serving as a fluorescent dye are connected via an amide bond, was designed and synthesized. The compound, in which the electron donating ability of the amino group at position 7 of AMC is lowered by connection of myristoyl asparagine, does not emit fluorescence. However, if the peptide bond moiety is cleaved by the enzyme encoded by ClbP gene of a colibactin biosynthetic gene cluster to produce a fluorescent dye, i.e., AMC, the presence or absence of the enzyme encoded by ClbP can be detected based on fluorescence emission. Thus, the compound can be used as a probe for detecting a colibactin biosynthetic gene cluster.

Synthesis of Probe 1

[Formula 19]

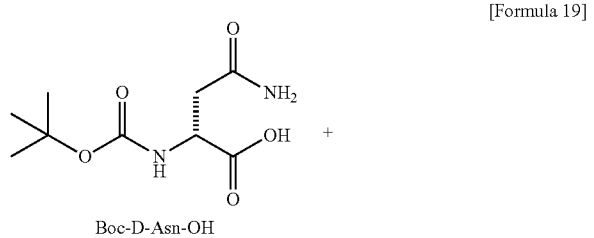

Boc-D-Asn-OH

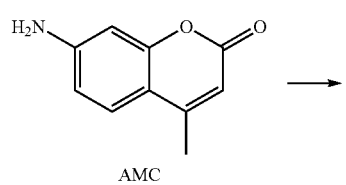

AMC

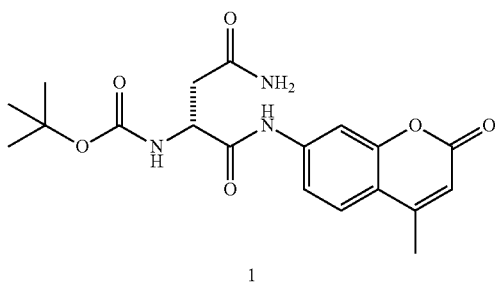

1

In a 50-mL eggplant flask, Boc-D-Asn-OH (300 mg (1.3 mmol)), 7-Amino-4-methylcoumarin (AMC) (176 mg (1.0 mmol)), O-(7-Aza-1H-benzotriazol-1-yl)-N,N,N',N'-tetramethyluronium hexafluorophosphate (HATU) (400 mg (1.1 mmol)) and N,N-dimethyl-4-aminopyridine (DMAP) (one piece (catalyst amount)) were weighed and added. After the air of the flask was replaced with nitrogen, dissolution with dry N,N-dimethylformamide (DMF) (5 mL) was carried out. N,N-diisopropylethylamine (DIEA) (1504 (0.9 mmol)) was added and the resultant mixture was stirred at room temperature for 4 days. After a saturated solution of sodium bicarbonate (35 mL) was added and sufficiently stirred, insoluble substances were filtered, and the filtrate was concentrated under reduced pressure by a vacuum line to obtain amide 1 in a yield of 26 mg (0.067 mmol, yield 6.7%).

[Formula 20]

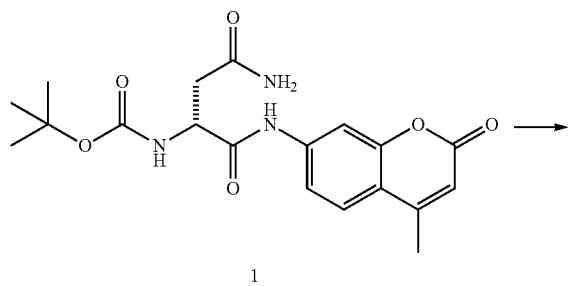

1

2

Amide 1 (26 mg (0.067 mmol)) was added in a 50-mL eggplant flask and dichloromethane (1 mL) and 1 mL of trifluoroacetic acid (TFA) were added. The reaction solution was stirred at room temperature for one hour, concentrated under reduced pressure and subjected twice to azeotropic distillation with toluene. The resultant crude Boc-deprotected form 2 was subjected to the following reaction as it was.

[Formula 21]

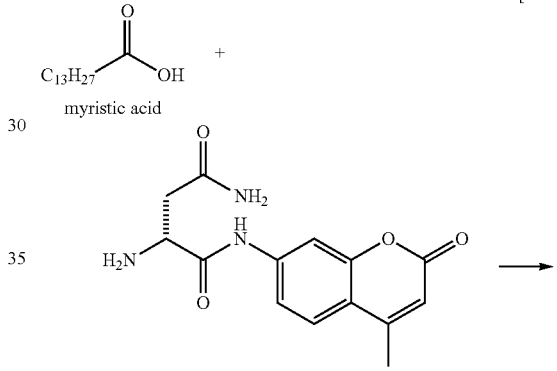

myristic acid

ClbP probe I

In a 50-mL eggplant flask, crude Boc-deprotected form 2, myristic acid (20 mg (0.088 mmol)) and HATU (30 mg (0.078 mmol)) were weighed and added. After the air of the flask was replaced with nitrogen, Dry DMF (1 mL) and DIEA (100 μL (0.57 mmol)) were added. The reaction solution was stirred at room temperature for 4 hours. To the reaction solution, a saturated solution of sodium bicarbonate (10 mL) was added. The resultant solution was extracted three times with ethyl acetate (50 mL). The organic layers obtained were combined and concentrated. The product obtained was purified by HPLC [5C18-MS-II (φ20×250 mm), acetonitrile-H₂O gradient 70-100% 1 h] to obtain probe 1 in a yield of 6 mg (0.012 mmol, two-stage recovery rate 18%).

Synthesis of Probe 2

[Formula 22]

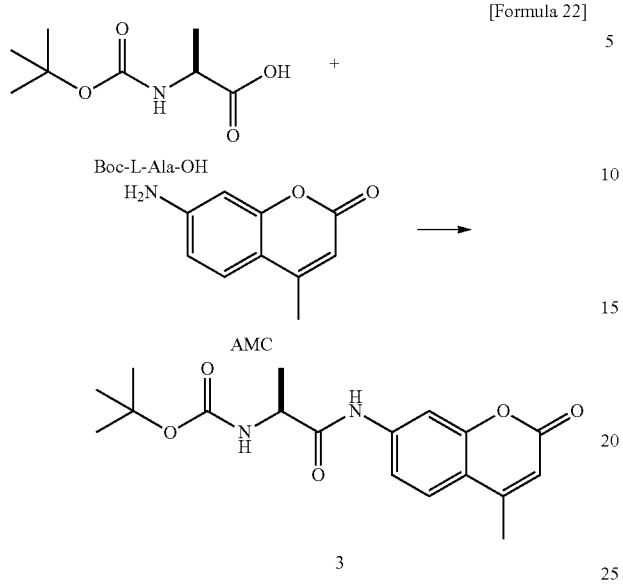

In a 30-mL eggplant flask, Boc-L-Ala-OH (98 mg (0.52 mmol)), AMC (60 mg (0.34 mmol)) and HATU (380 mmol (1.0 mmol)) were weighed and added. After the air of the flask was replaced with nitrogen, Dry DMF (2 mL), DIEA (200 µL (1.15 mmol)) and DMAP (catalyst amount) were added. The reaction solution was stirred at room temperature for a day. To the reaction solution, a saturated solution of sodium bicarbonate (8 mL) was added. The resultant solution was extracted three times with 5 mL of ethyl acetate/hexane (4/1). The organic layers obtained were combined, washed once with saturated saline (5 mL), concentrated under reduced pressure to obtain a crude product (240 mg). The crude product was purified by silica gel column chromatography [manufactured by Kanto Chemical Co., Inc., Silica Gel 60N 100-210 µm 5 g (chloroform/methanol=1/0→30/1→15/1)] and HPLC [5C18-MS-II (φ20×250 mm), 45% acetonitrile-H$_2$O] to obtain amide 3 in a yield of 91 mg (0.26 mmol, yield 76%).

[Formula 23]

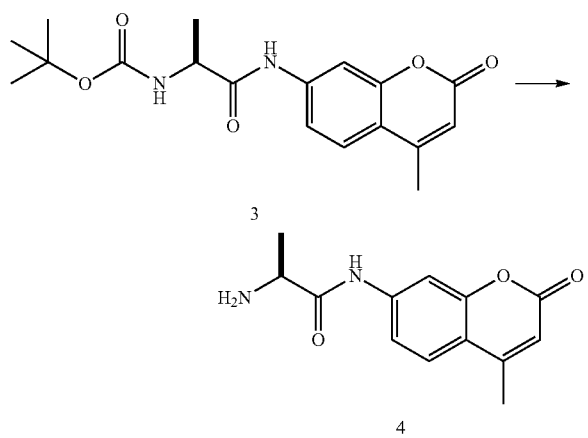

In a 30 mL eggplant flask, amide 2 (21 mg (0.062 mmol)) was weighed and added. To the flask, dichloromethane (0.5 mL) and TFA (0.5 mL) were added. The reaction solution was stirred at room temperature for one hour. The resultant reaction solution was concentrated under reduced pressure and subjected five times to azeotropic distillation with toluene to obtain crude Boc-deprotected form 4. The resultant crude Boc-deprotected form 4 were subjected to the following reaction as it was.

[Formula 24]

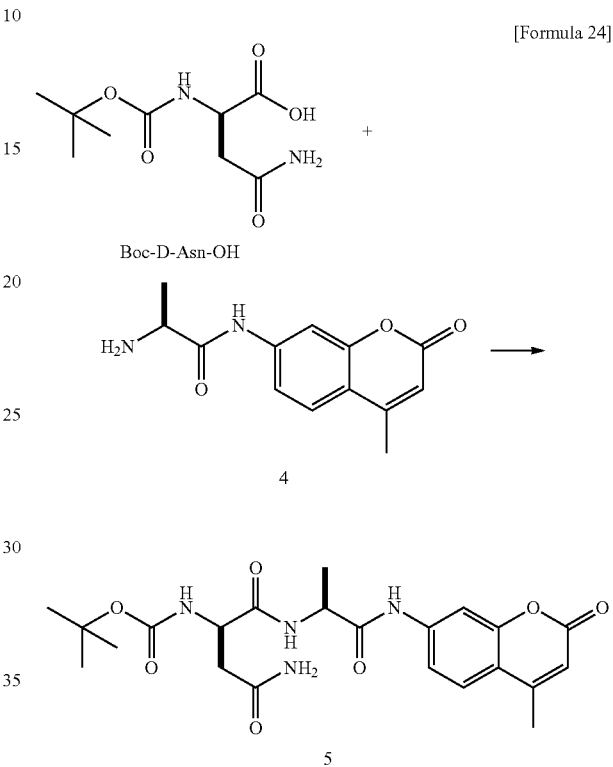

In a 30-mL eggplant flask, crude Boc-deprotected form 4, Boc-D-Asn-OH (20 mg (0.088 mmol)) and HATU (25 mg (0.067 mmol)) were added. After the air of the flask was replaced with nitrogen, dissolution with Dry DMF (1 mL) was carried out. DIEA (100 µL (0.58 mmol)) was added, stirring was carried out at room temperature for 11 hours. To the resultant reaction solution, a saturated solution of sodium bicarbonate (5 mL) was added. The resultant solution was extracted 4 times with ethyl acetate (5 mL). The organic layers obtained were combined, dried over sodium sulfate and concentrated. Further, H$_2$O (5 mL) was added and lyophilization was carried out to obtain crude amide 5 in a yield of 39 mg. The amide 5 thus obtained was subjected to the following reaction, as it was.

[Formula 25]

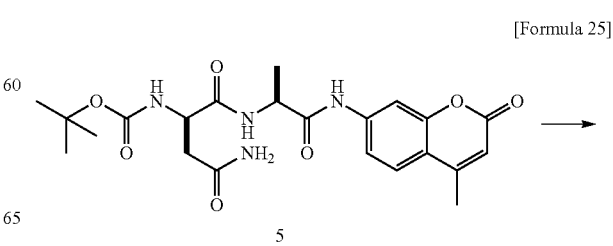

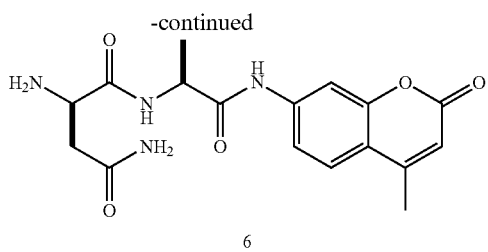

6

In a 30-mL eggplant flask, crude amide 5 (39 mg), dichloromethane (0.5 mL) and TFA (0.5 mL) were weighed and added. The reaction solution was stirred at room temperature for one hour. The reaction solution was concentrated under reduced pressure and subjected twice to azeotropic distillation with toluene. The crude Boc-deprotected form 6 was subjected to the following reaction, as it was.

[Formula 26]

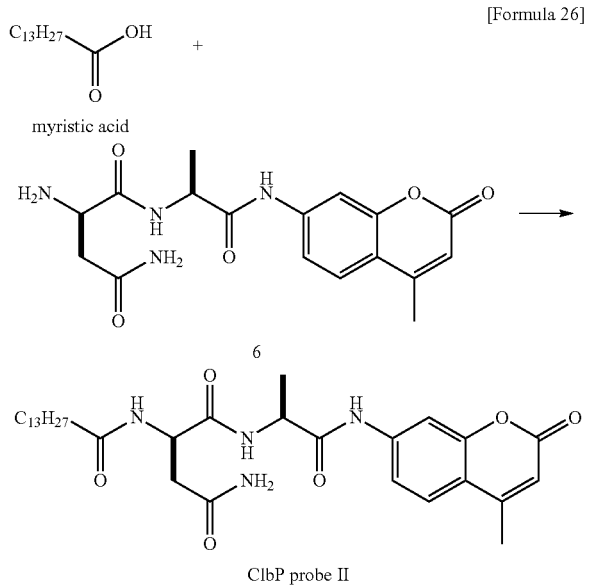

ClbP probe II

In a 30-mL eggplant flask, crude Boc-deprotected form 6, myristic acid (20 mg (0.087 mmol)) and HATU (25.1 mg (0.066 mmol)) were weighed and added. After the air of the flask was replaced with nitrogen, Dry DMF (1 mL) was added. After DIEA 100 μL (0.58 mmol) was added, the reaction solution was stirred at room temperature for 3 hours. To the reaction solution, a saturated solution of sodium bicarbonate (10 mL) was added, and insoluble substances were separated by filtration and washed with a saturated solution of sodium bicarbonate and water. The remaining insoluble substances were collected. The DMF soluble matter was purified by HPLC [5C18-MS-II (φ20× 250 mm), acetonitrile-H$_2$O gradient 50-100% 1 h] to obtain ClbP probe II (3.8 mg (6.7 μmol, 4-step yield: 11%)).

Example 3: Detection of *Escherichia coli* Having Colibactin Production System in Biological Sample As a biological sample, patient's feces samples, which were found to have a colibactin biosynthetic gene cluster in Example 1, were used.

Figure 2:
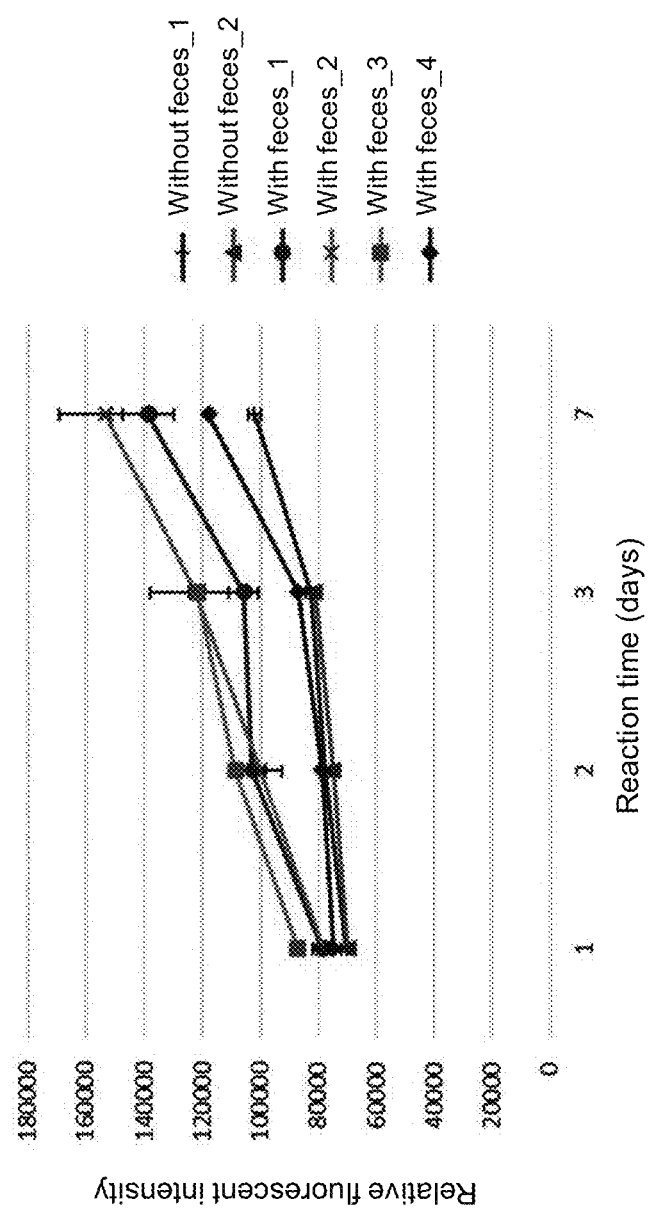
FIG. 2 is a graph showing that fluorescence was emitted from a fluorescent probe of the present invention in a ClbP (in dry fecal sample) dependent manner.

The feces samples (obtained from different 4 human subjects) lyophilized were each scooped 10 times by a spoon (about 40 mg) and suspended in milliQ water (200 μl). To the suspension, the 20 mM DMSO solution of probe 1 was added so as to obtain a final concentration of 20 μM (DMSO final concentration 0.1%). Thereafter, the suspension was shaken at 37° C. and 100 rpm for 24 hours or more. After the reaction, the reaction solution (200 μLS) was taken and centrifuged. The supernatant (200 μL) was directly subjected to detection performed at $\lambda_{ex}$380 mm/$\lambda_{em}$460 mm (unextracted). The reaction solution (200 μL) was newly taken, sufficiently suspended by adding ethyl acetate (500 μL) and centrifuged. The ethyl acetate layer (450 μL) of the supernatant was collected and concentrated. To the concentrate, milliQ water (200 μL) was added. The mixture was sufficiently suspended and centrifuged. The supernatant (200 μL) was subjected to detection performed at $\lambda_{ex}$380 mm/$\lambda_{em}$460 mm (after extraction). The results were as shown in FIG. 2. In FIG. 2, the detection results of 4 fecal samples are shown separately by "feces is present_1" to "feces is present_4", respectively.

As shown in FIG. 2, it was exhibited that fluorescence was regained by bringing the probe into contact with feces. This means that the enzyme encoded by ClbP gene is present in the feces; more specifically, the probe was cleaved by the enzyme to produce fluorescent AMC. As a result, it was demonstrated that *Escherichia coli* having a colibactin biosynthetic gene cluster present in fecal samples can be detected based on the fluorescence intensity of the probe (designed above) as an index. The same results as shown in FIG. 2 were obtained in the cases of unextracted fecal samples. As a result, it was found that the enzyme encoded by ClbP gene may not be extracted when fecal samples are analyzed. The same results are obtained in the case of probe 2 obtained in Example 1.

A fecal sample may be cultured in the conditions suitable for proliferation of *Escherichia coli* and then subjected to analysis. According to the Example, since the amount of colibactin-producing *Escherichia coli* increases by culturing, the detection sensitivity for colibactin and a colibactin-producing bacterium were improved.

Example 4: Assay Using Cultured *Escherichia coli*

In this Example, investigation was made as to whether only colibactin-producing *Escherichia coli* can be detected by the probe from *Escherichia coli* producing colibactin and *Escherichia coli* not producing colibactin.

As *Escherichia coli* not producing colibactin, 1246 strain and 1649T strain were used. As the colibactin-producing *Escherichia coli*, 5263 strain, 5491 strain and Nissle strain were used.

*Escherichia coli* were cultured overnight and seeded (20 μL) in LB medium (2 to 4 mL) and further a 20 mM DMSO solution of probe 1 was added thereto so as to obtain a final concentration of 20 μM (DMSO final concentration: 0.1%), and cultured at 37° C. and 100 rpm for 24 hours or more while shaking. After reaction, the reaction solution (200 μL) was taken and centrifuged. The supernatant (200 μL) was directly subjected to detection performed at $\lambda_{ex}$ 380 mm/$\lambda_{em}$ 460 mm (unextracted). The reaction solution (200 μL) was newly taken and ethyl acetate (500 μL) was added thereto. After sufficiently suspended, the suspension was centrifuged. The ethyl acetate layer (450 μL) of the supernatant was recovered and concentrated. To the concentrate, milliQ water (200 μL) was added. The mixture was sufficiently suspended and centrifuged. The supernatant (200 μL) was subjected to detection (after extraction) performed at $\lambda_{ex}$ 380 mm/$\lambda_{em}$ 460 mm. The results were as shown in FIG. 3.

Figure 3:
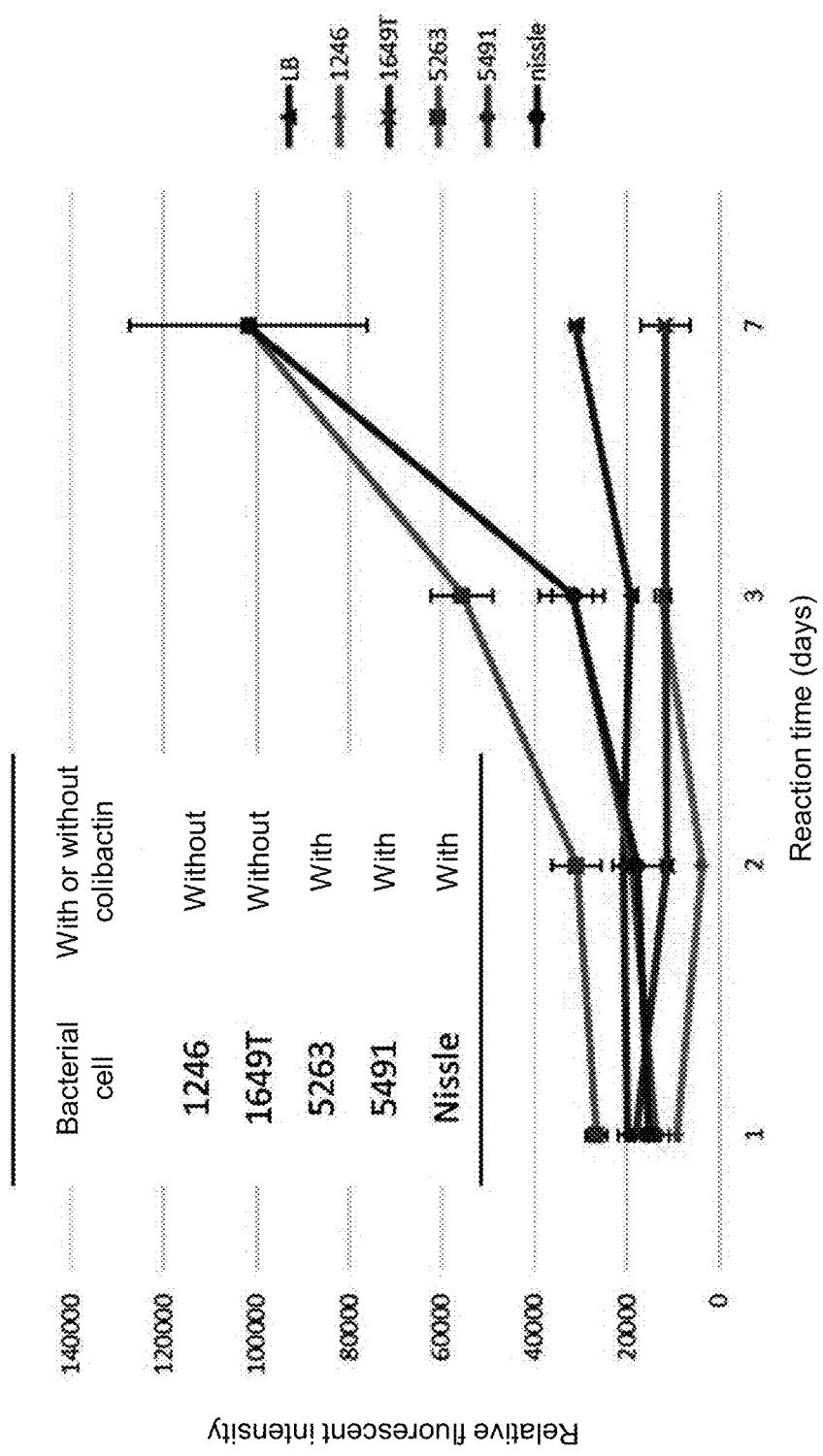
FIG. 3 is a graph showing that fluorescence was emitted from a fluorescent probe of the present invention in a colibactin-producing bacterium (in dry fecal sample) dependent manner.

As shown in FIG. 3, it was found that colibactin-producing Escherichia coli can be detected particularly in the sample "after extraction" based on the fluorescence intensity of a probe as an index by using the above detection system. The same results were obtained when probe 2 prepared in Example 1 was used.

Example 5: Detection of Colibactin Positive Bacterium from Escherichia coli Separated from Colorectal Tissue Samples In this Example, detection of a colibactin positive bacterium was tried by applying probe I to Escherichia coli bacteria separated from colon tissue samples (n=100) in which colibactin biosynthetic genes had been detected by PCR methods and colon tissue samples (n=100) in which colibactin biosynthetic genes had not been detected.

Escherichia coli bacteria were separated by homogenizing a human colorectal tissue sample with physiological saline and smearing the homogenized sample onto a MacConkey plate medium, and culturing it. To check whether Escherichia coli bacterium having a colibactin production system is present in the sample, clbB (gene) of the colibactin biosynthetic gene cluster was amplified by PCR using the following primers. Based on the presence or absence of an amplified fragment as an index, a colibactin positive bacterium or not was evaluated.

```
clbB forward primer
                          (SEQ ID NO: 7)
tgttccgttttgtgtggtttcagcg clbB reverse primer
                          (SEQ ID NO: 8)
gtgcgctgaccattgaagatttccg
```

To evaluate the sensitivity and accuracy for detecting a colibactin positive bacterium by probe I, 100 Escherichia coli bacterium samples were prepared by separating Escherichia coli bacterium from colon tissue samples in which a colibactin positive bacterium was detected by the above PCR method; and 100 Escherichia coli bacterium samples separated were prepared by separating Escherichia coli bacterium from colon tissue samples in which a colibactin positive bacterium was not detected by the above PCR method. LB liquid medium (100 µL) (assay A) comprising 100 µM probe and 100 µL of LB liquid medium (assay B) not comprising a probe were dispensed separately to individual wells of 96 well plates. A single colony of Escherichia coli strain on the plate medium was picked up by a toothpick (extremely small amount of bacterial cells) and added to individual wells for assay A and assay B. The plates were allowed to stand still at 37° C. for 24 hours for culture and thereafter fluorescence was measured. Measurement at $\lambda_{ex}$ 380 mm/$\lambda_{em}$ 460 mm was carried out by a plate reader. The difference in fluorescence intensity between assay A and assay B (background) was obtained and the threshold was determined as 100. The case where the ratio is more than 100 was determined as a positive; whereas, the case where the ratio is less than 100 was determined as a negative.

Figure 4:
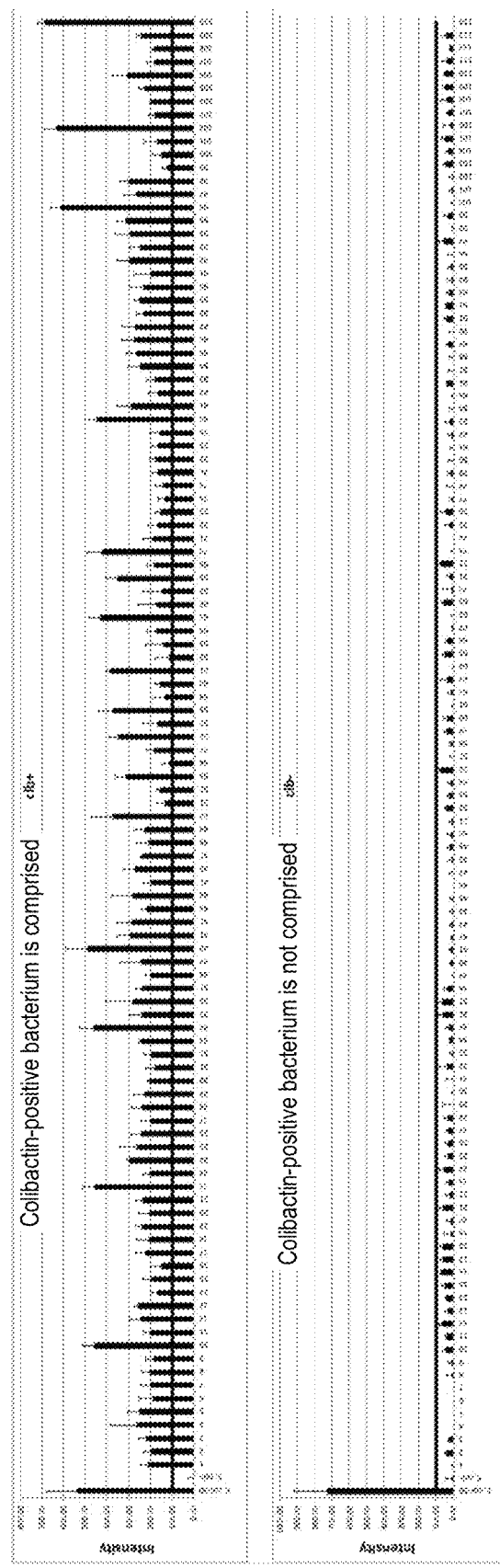
FIG. 4 shows the detection results of *Escherichia coli* isolated from a human colorectral tissue sample by a probe of the present invention. The vertical axis represents the intensity of fluorescence from probe I; whereas, the horizontal axis represents individual samples. The upper graph of FIG. 4 shows the intensity of fluorescence from probe I for samples determined by a PCR method as comprising colibactin positive bacterium, whereas, the lower graph of FIG. 4 shows the intensity of fluorescence from probe I versus samples determined by a PCR method as not comprising a colibactin positive bacterium. The leftmost bar chart of each of the upper and lower graphs in FIG. 4 shows a positive control and the adjacent bar chart shows a negative control.

The results were as shown in FIG. 4. In FIG. 4, the upper graph shows 100 samples, in which a colibactin positive bacterium was detected by PCR. The lower graph shows 100 samples, in which a colibactin positive bacterium was not detected by PCR. The vertical axis represents the fluorescence intensity ($\lambda_{ex}$ 380 mm/$\lambda_{em}$ 460 mm) and the horizontal axis represents individual samples. As shown in FIG. 4, probe I detects a colibactin positive bacterium with an accuracy of 100% and a false positive rate (a rate determining a negative bacterium as a positive bacterium) was less than 1%. Note that, the leftmost bar chart of each of the upper and lower graphs in FIG. 4 shows a positive control and the adjacent bar chart shows a negative control.

From the results, it was confirmed that the probe of the present invention is useful for detecting colibactin-positive bacterium.

Example 6: Detection of Colibactin Positive Bacterium Using Fecal Sample

In this Example, it was confirmed that a colibactin positive bacterium can be detected by dissolving a fecal sample in water, culturing, and applying probe I to the obtained culture.

Fecal samples obtained from human subjects were dissolved in water, applied to a plate comprising a MacConkey medium and cultured at 37° C. for 12 hours. The resultant red-purple colony was picked up, inoculated in LB liquid medium comprising 100 µM probe I and cultured for 24 hours. Fluorescence ($\lambda_{ex}$ 380 mm/$\lambda_{em}$ 460 mm) was measured by a plate reader. These samples were checked for the presence or absence of a colibactin positive bacterium by a PCR method in the same manner as in Example 5 and the correlation with the fluorescence intensity generated from probe I was examined. The results were as shown in FIG. 5.

Figure 5:
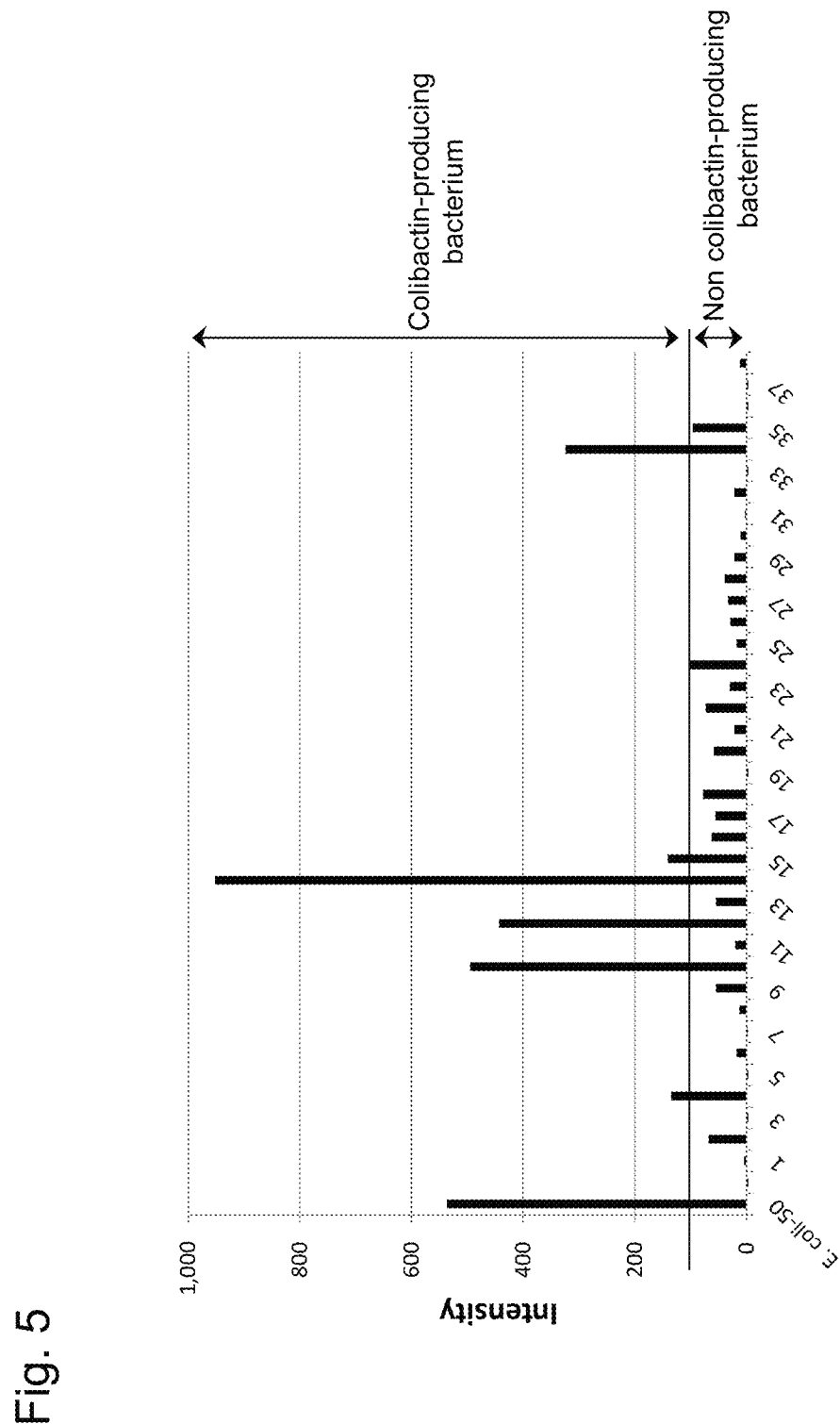
FIG. 5 shows the intensity of fluorescence from probe I for cultures obtained by culturing *Escherichia coli* isolated from human fecal samples. The vertical axis represents the intensity of fluorescence from probe I; whereas, the horizontal axis represents the individual samples. The leftmost bar chart shows a positive control; whereas the rightmost bar chart shows a negative control.

As shown in FIG. 5, the colibactin positive bacterium present in fecal samples can be highly sensitively and accurately detected by probe I Example 7: Detection of Colibactin Positive Bacterium in Cancer Patient's Tissue Stored in Frozen State In the Example, a colorectal cancer tissue and tissue including the peripheral tissue thereof stored in a frozen state were checked for colibactin biosynthetic genes by a PCR method. Thereafter, a homogenization solutions of the tissues were cultured. The amounts of myristoyl-D-asparagine comprised in the obtained cultures were quantified.

As a result, in the samples derived from the total 14 subjects, a colibactin biosynthetic gene was detected in 8 (57.1%) cancer-tissue samples and a single (7.1%) normal tissues sample (see FIG. 6). The homogenization solutions of the above tissues were applied to MacConkey agar medium and bacteria that can be cultured were obtained from the medium. The presence or absence of a colibactin biosynthetic gene in the colonies obtained was checked by a colony PCR method. As a result, 36 out of total 220 colonies derived from cancer tissues were positive to a colibactin biosynthetic gene (16.4%) (see, FIG. 6). In contrast, only one out of 103 colonies derived from the normal tissue was colibactin biosynthetic gene positive (0.9%).

From the foregoing, it was suggested that many colibactin producing bacteria are present in the colorectal cancer tissue. The colibactin biosynthetic gene positive 37 strains (in total) obtained were cultured in vitro, and the amount of myristoyl-D-asparagine was measured. Based on the amount of myristoyl-D-asparagine, colibactin production ability was evaluated. The results were as shown in FIG. 7. As shown in FIG. 7, production of myristoyl-D-asparagine was confirmed in 36 of the total 37 strains except H13-3310T-16, in which the production was a detection limit or less. The production amount clearly differs between the strains. The production amount of a strain exhibiting a high productivity was about 10,000 times as large as that of a strain exhibiting a low productivity.

The invention claimed is:

1. A compound or a fluorescent probe selected from the group consisting of:
   (A) a compound or a fluorescent probe obtained by connecting an amino group of a coumarin fluorescent dye having the amino group at position 7 of a coumarin skeleton and a carboxyl group of myristoyl asparagine via an amide bond;
   (B) a compound or a fluorescent probe obtained by connecting an amino group of a naphthalimide fluorescent dye having the amino group at position 4 of a naphthalimide skeleton and a carboxyl group of myristoyl asparagine via an amide bond;
   (C) a compound or a fluorescent probe obtained by connecting an amino group of naphthalene, pyrene or anthracene having the amino group at position 2 thereof and a carboxyl group of myristoyl asparagine via an amide bond;
   (D) a compound or a fluorescent probe obtained by connecting one or both of amino groups of a rhodamine fluorescent dye having the amino group at position 3 and/or 9 of a xanthene skeleton and carboxyl group(s) of myristoyl asparagine via an amide bond;
   (E) a compound or a fluorescent probe obtained by connecting one or both of amino groups of Bodipy fluorescent dye having the amino group at position 1 and/or 7 of Bodipy mother nucleus and the carboxyl group(s) of myristoyl asparagine via an amide bond;
   (F) a compound or a fluorescent probe obtained by connecting said carboxyl group and said amino group in any one of (A) to (E) via alanine (—NH—CH(CH3)-CO—) (each forms an amide bond with alanine);
   (G) a compound or a fluorescent probe obtained by connecting a carboxyl group of myristoyl asparagine and a hydroxyl group of oFlu, which is a fluorescent group that exhibits fluorescence when the hydroxyl group is released, via a self-cleavable linker, wherein the selfcleavable linker is connected to the carboxyl group of myristoyl asparagine via an amide bond; and the hydroxyl group of oFlu is liberated when the amide bond is decomposed by hydrolysis; and
   (H) a compound or fluorescent probe having a fluorescent dye connected to a carboxyl group of myristoyl asparagine via an amide bond, wherein fluorescence is emitted after the amide bond is cleaved in a ClbP dependent manner.

2. The compound or the fluorescent probe according to claim 1, wherein the compound or the fluorescent probe is (A) a compound or a fluorescent probe obtained by connecting an amino group of a coumarin fluorescent dye having the amino group at position 7 of a coumarin skeleton and a carboxyl group of myristoyl asparagine via an amide bond.

3. The compound or the fluorescent probe according to claim 1, wherein the compound or the fluorescent probe is (B) a compound or a fluorescent probe obtained by connecting an amino group of a naphthalimide fluorescent dye having the amino group at position 4 of a naphthalimide skeleton and a carboxyl group of myristoyl asparagine via an amide bond.

4. The compound or the fluorescent probe according to claim 1, wherein the compound or the fluorescent probe is (C) a compound or a fluorescent probe obtained by connecting an amino group of naphthalene, pyrene or anthracene having the amino group at position 2 thereof and a carboxyl group of myristoyl asparagine via an amide bond.

5. The compound or the fluorescent probe according to claim 1, wherein the compound or the fluorescent probe is (D) a compound or a fluorescent probe obtained by connecting one or both of amino groups of a rhodamine fluorescent dye having the amino group at position 3 and/or 9 of a xanthene skeleton and carboxyl group(s) of myristoyl asparagine via an amide bond.

6. The compound or the fluorescent probe according to claim 1, wherein the compound or the fluorescent probe is (E) a compound or a fluorescent probe obtained by connecting one or both of amino groups of Bodipy fluorescent dye having the amino group at position 1 and/or 7 of Bodipy mother nucleus and the carboxyl group(s) of myristoyl asparagine via an amide bond.

* * * * *